(12) United States Patent
Hasan et al.

(10) Patent No.: US 9,968,767 B1
(45) Date of Patent: May 15, 2018

(54) COMBINATION MICROARRAY PATCH FOR DRUG DELIVERY AND ELECTROCHEMOTHERAPY DEVICE

(71) Applicant: KING SAUD UNIVERSITY, Riyadh (SA)

(72) Inventors: Sartaj Tabassum Hasan, Riyadh (SA); Hamad A. Al-Lohedan, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days. days.

(21) Appl. No.: 15/729,490

(22) Filed: Oct. 10, 2017

(51) Int. Cl.
*A61M 37/00* (2006.01)
*A61N 1/32* (2006.01)
*A61N 1/04* (2006.01)

(52) U.S. Cl.
CPC ....... *A61M 37/0015* (2013.01); *A61N 1/0416* (2013.01); *A61N 1/327* (2013.01); *A61M 2037/0007* (2013.01); *A61M 2037/0023* (2013.01)

(58) Field of Classification Search
CPC ...... A61M 37/0015; A61M 2037/0023; A61M 2037/0007; A61N 1/0416; A61N 1/327
See application file for complete search history.

(56) References Cited

U.S. PATENT DOCUMENTS

| 7,108,681 | B2 | 9/2006 | Gartstein et al. |
| 8,075,826 | B2 | 12/2011 | Lastovich et al. |
| 2004/0236271 | A1 * | 11/2004 | Theeuwes ......... A61M 37/0015 604/47 |
| 2008/0312610 | A1 | 12/2008 | Binks et al. |
| 2014/0046293 | A1 | 2/2014 | Hattersley et al. |
| 2017/0028184 | A1 | 2/2017 | Gooden et al. |
| 2017/0050010 | A1 | 2/2017 | McAllister et al. |

FOREIGN PATENT DOCUMENTS

KR 020090079714 A 7/2009

OTHER PUBLICATIONS

Haripriya Kalluri et al., "Transdermal Delivery of Proteins," AAPS PharmSciTech, vol. 12, No. 1, Mar. 2011.

* cited by examiner

*Primary Examiner* — Emily Schmidt
*Assistant Examiner* — Amber Stiles
(74) *Attorney, Agent, or Firm* — Richard C. Litman

(57) ABSTRACT

The combination microarray patch for drug delivery and electrochemotherapy device is a medical device for delivering two separate pharmaceutical preparations to a patient, as well as providing electrostimulation for electroactive pharmaceuticals. A first pharmaceutical preparation is manually delivered into the patient through a first set of drug delivery needles. Similarly, a second pharmaceutical preparation is manually delivered into a patient through a second set of drug delivery needles. A desired electrical potential may then be selectively applied across first and second sets of electrotherapy needles for electroporation to facilitate delivery of the pharmaceutical preparations. The second pharmaceutical preparation may be a conjugate of the first for targeted drug delivery.

8 Claims, 4 Drawing Sheets

COMBINATION MICROARRAY PATCH FOR DRUG DELIVERY AND ELECTROCHEMOTHERAPY DEVICE

BACKGROUND OF THE INVENTION

1. Field of the Invention

The disclosure of the present patent application relates to medical treatment, and particularly to a combination microarray patch for drug delivery and electrochemotherapy device that is capable of delivering two separate pharmaceutical preparations to a patient and providing electroporation to facilitate delivery of the drugs.

2. Description of the Related Art

Electrochemotherapy is a type of chemotherapy that allows delivery of non-permeant drugs to the cell interior. It is based on the local application of short and intense electric pulses that transiently permeabilize the cell membrane, thus allowing transport of molecules otherwise not permitted by the membrane. All present biomedical applications of cell electropermeabilization use direct currents with short and intense pulses. The amplitude of the pulses depends on the tissues and on the shape and position of the electrodes.

Electrochemotherapeutic treatment consists of delivering, either systemically or locally, non-permeant cytotoxic drugs (e.g., bleomycin) or low-permeant drugs (e.g., cisplatin) and applying electric pulses to the area to be treated when the concentration of the drug in the tumor is at its peak. With the delivery of the electric pulses, cells are subjected to an electric field that causes the formation of nanoscale defects on the cell membrane, which alter the permeability of the membrane. At this stage and for some time after pulses are delivered, molecules of the cytotoxic agents can freely diffuse into the cytoplasm and exert their cytotoxic effect.

Presently, a desired chemotherapy drug is delivered to the patient via conventional delivery, and then an electrochemotherapy device is applied to the patient to generate the desired current at the site of treatment. Thus, the patient typically has to undergo two or more applications of needles (a typical electrochemotherapy device has needles which pierce the skin to deliver the current) during a single treatment session. The number of needle applications increases with each additional drug used, thus potentially increasing pain and discomfort to the patient through not only successive needle insertions, but also drawn out over time for each needle insertion and removal. Thus, a combination microarray patch for drug delivery and electrochemotherapy device solving the aforementioned problems is desired.

SUMMARY OF THE INVENTION

The combination microarray patch for drug delivery and electrochemotherapy device is a medical device capable of delivering two separate pharmaceutical preparations to a patient, as well as providing electroporation to facilitate delivery of the drugs. The combination microarray patch for drug delivery and electrochemotherapy device includes a hollow housing having a lower wall, an upper wall and at least one sidewall. The upper wall is flexible, allowing drug delivery to be performed manually.

At least one inner wall is disposed within the hollow housing. The at least one inner wall divides an interior region of the hollow housing into an inner reservoir and an outer reservoir. Preferably, the inner and outer receptacles are fluidly sealed with respect to one another. The inner receptacle is adapted for receiving a first pharmaceutical preparation and the outer receptacle is adapted for receiving a second pharmaceutical preparation.

An anode and a cathode are each disposed within the hollow housing and are adapted for selective communication with an external electrical power supply, an on-board battery or the like. The anode and the cathode are preferably each respectively received in one of a pair of fluid-tight chambers defined in the hollow housing.

A first set of drug delivery needles is mounted to the lower wall of the hollow housing and projects outward therefrom. The first set of drug delivery needles is in fluid communication with the inner receptacle for selective delivery of the first pharmaceutical preparation to the patient. Similarly, a second set of drug delivery needles is mounted to the lower wall of the hollow housing and also projects outward therefrom. The second set of drug delivery needles is in fluid communication with the outer receptacle for selective delivery of the second pharmaceutical preparation to the patient.

First and second sets of electrotherapy needles are also mounted to the lower wall of the hollow housing and project outward therefrom. The first set of electrotherapy needles is in electrical communication with the anode and the second set of electrotherapy needles is in electrical communication with the cathode.

In use, the combination microarray patch for drug delivery and electrochemotherapy device is pressed against the skin of the patient at the desired drug delivery site such that the first and second sets of drug delivery needles and the first and second sets of electrotherapy needles pierce the patient's skin. The medical practitioner then depresses a first region of the flexible upper wall of the hollow housing, which is positioned above the inner receptacle, to deliver the first pharmaceutical preparation into the patient through the first set of drug delivery needles. The medical practitioner depresses a second region of the flexible upper wall of the hollow housing, which is positioned above the outer receptacle, to deliver the second pharmaceutical preparation into the patient through the second set of drug delivery needles. It should be understood that the first and second pharmaceutical preparations may be delivered simultaneously. A desired electrical potential may then be selectively applied across the anode and the cathode for electroporation to facilitate delivery of one or both of the pharmaceutical preparations.

These and other features of the present invention will become readily apparent upon further review of the following specification.

DETAILED DESCRIPTION OF THE PREFERRED EMBODIMENTS

Figure 1:
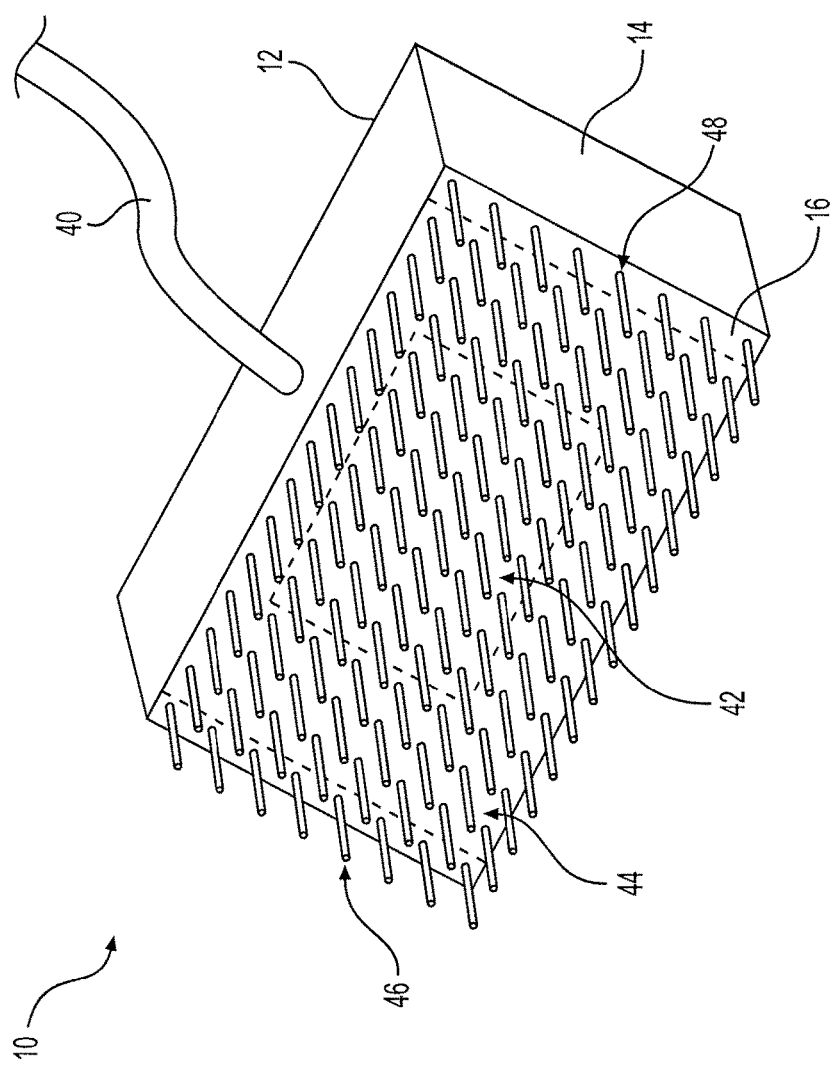
FIG. 1 is a perspective view of a combination microarray patch for drug delivery and electrochemotherapy device, showing a bottom view of the device.
Figure 2:
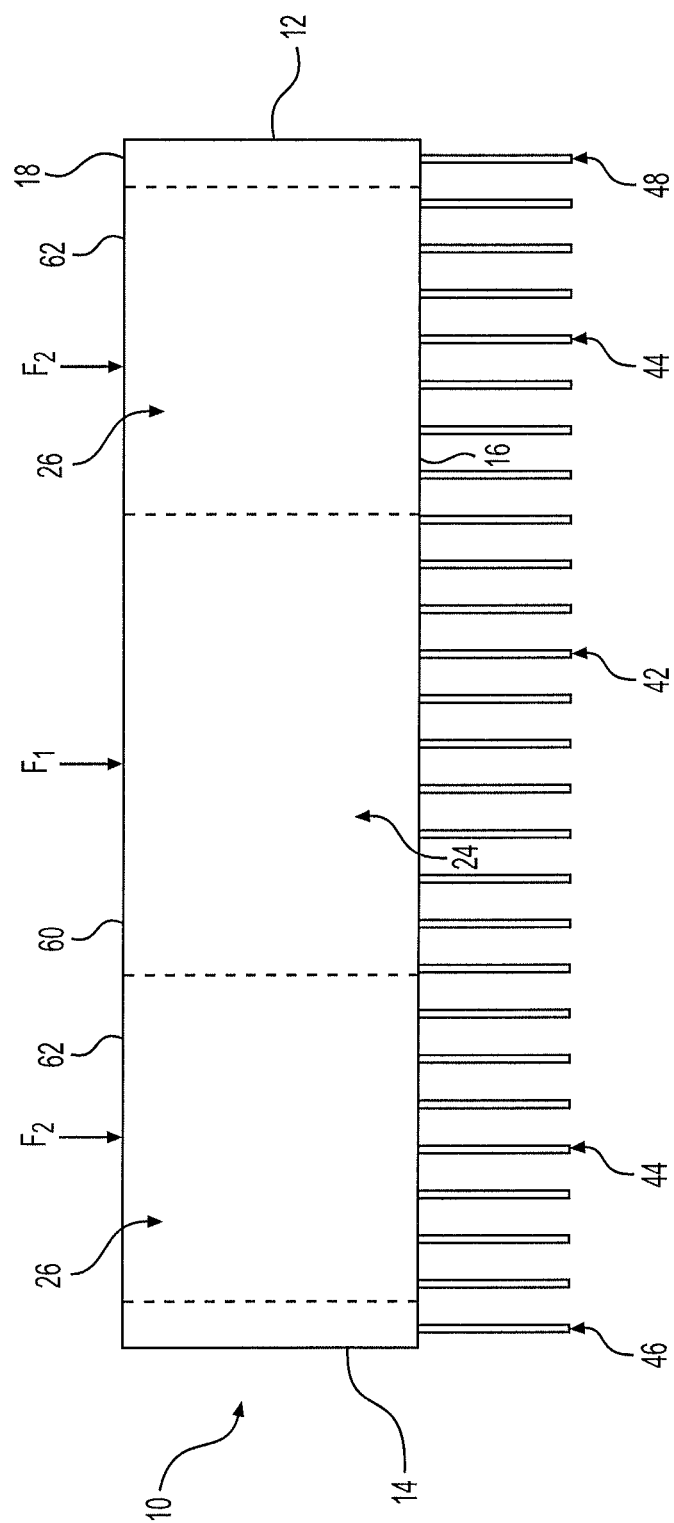
FIG. 2 is a front view of the combination microarray patch for drug delivery and electrochemotherapy device of FIG. 1.

The combination microarray patch for drug delivery and electrochemotherapy device 10 is a medical device capable of delivering two separate pharmaceutical preparations to a patient, as well as providing electrostimulation for electroactive pharmaceuticals. As shown in FIGS. 1-4, the combination microarray patch for drug delivery and electrochemotherapy device 10 includes a hollow housing 12 having a lower wall 16, an upper wall 18 and at least one sidewall 14 extending around the perimeter of the housing 12 between the lower wall 16 and the upper wall 18. In FIGS. 1-4, the at least one sidewall 14 is shown as having a substantially rectangular configuration. It should be understood that the overall configuration and relative dimensions of hollow housing 12 are shown for exemplary purposes only. The upper wall 18 is flexible, allowing drug delivery to be performed manually by a medical practitioner, as will described in greater detail below. It should be understood that lower wall 16 and the at least one sidewall 14 may be constructed from any suitable materials, such as rigid plastic, titanium or the like.

Figure 3:
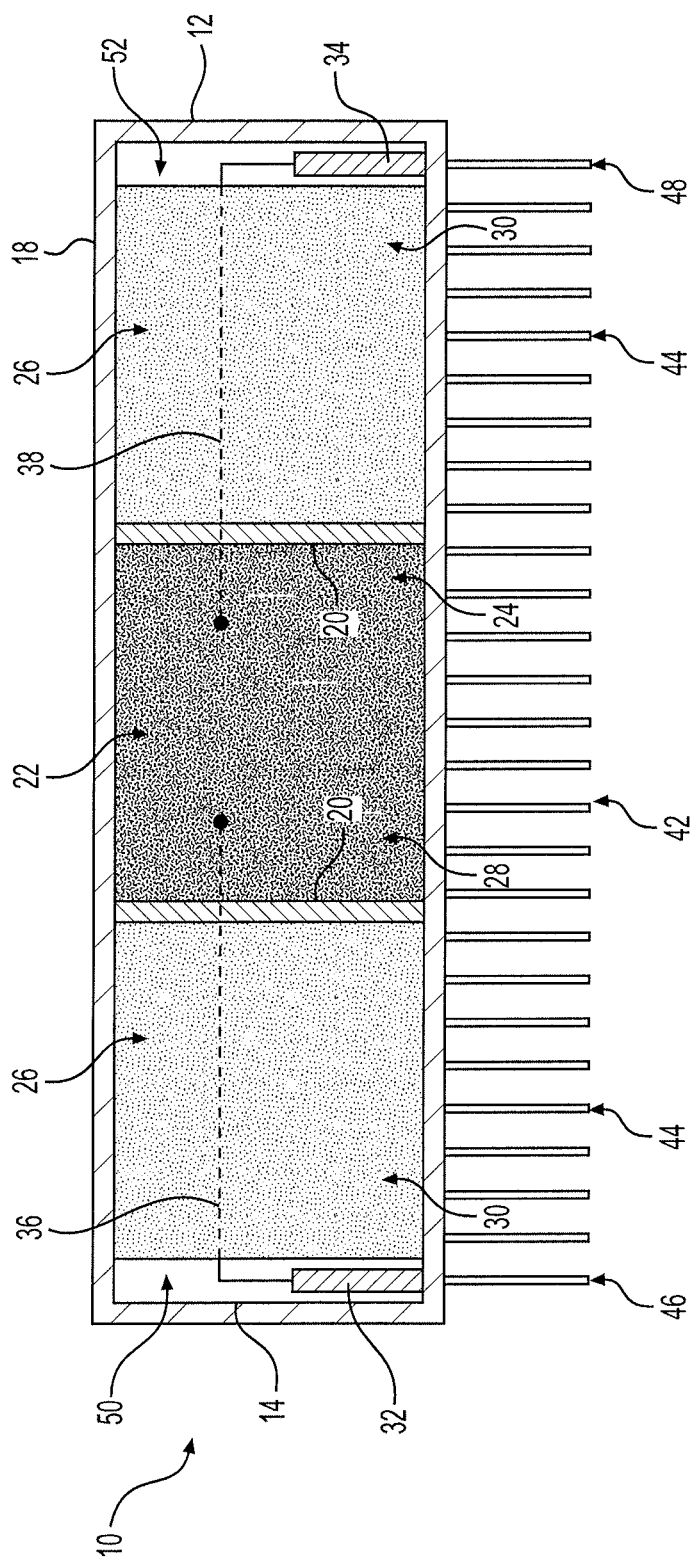
FIG. 3 is a front view in section of the combination microarray patch for drug delivery and electrochemotherapy device of FIG. 1.
Figure 4:
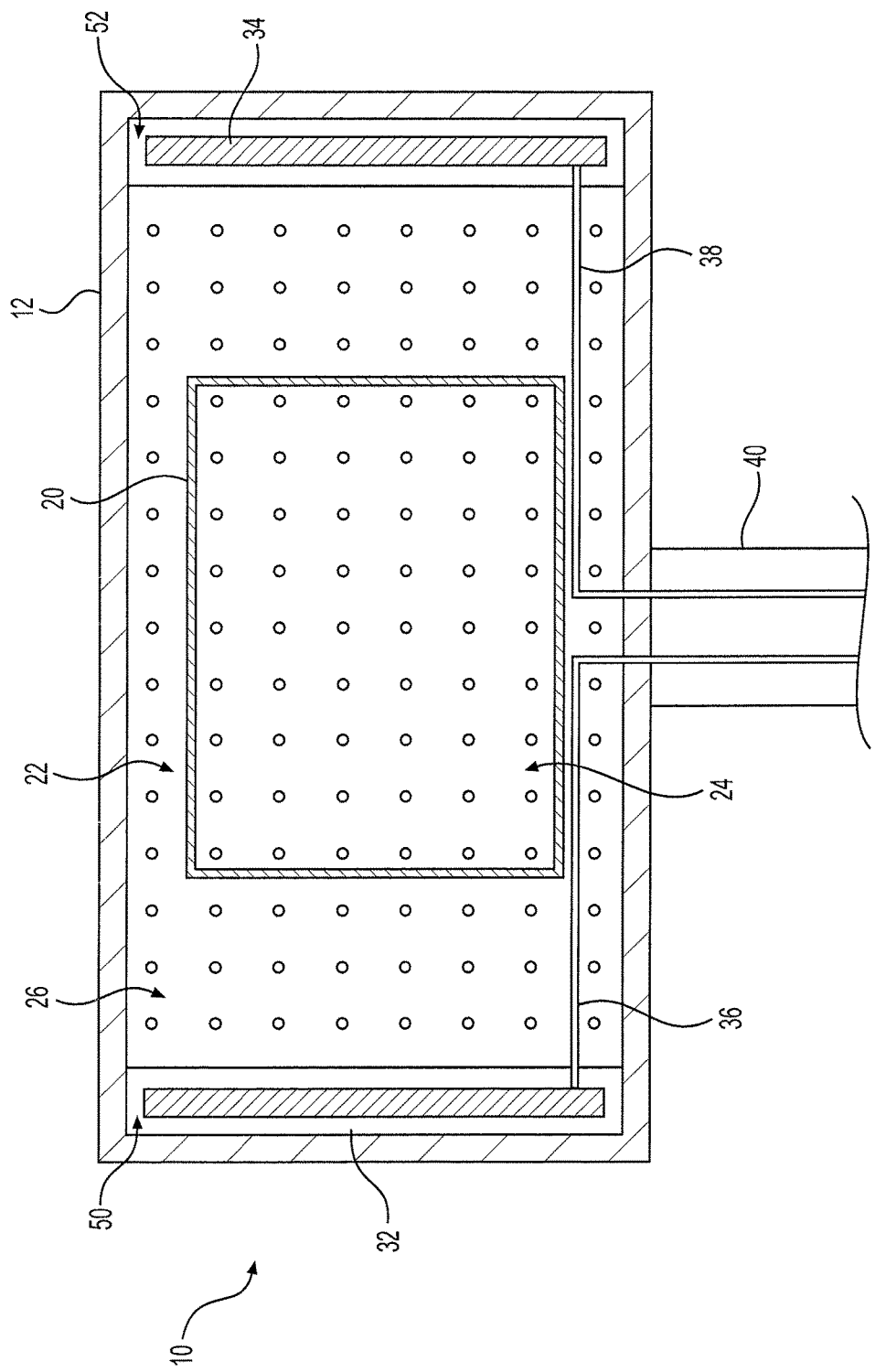
FIG. 4 is a top view in section of the combination microarray patch for drug delivery and electrochemotherapy device of FIG. 1.

As best shown in FIGS. 3 and 4, at least one inner wall 20 is disposed within the hollow housing 12. Although the at least one inner wall 20 is shown as having a rectangular configuration, matching that of exemplary hollow housing 12, it should be understood that the overall dimensions and configuration of the at least one inner wall 20 are shown for exemplary purposes only. As shown, the at least one inner wall 20 divides an interior region 22 of the hollow housing 12 into an inner drug reservoir 24 and an outer drug reservoir 26. Preferably, the inner and outer reservoirs 24, 26, respectively, are fluidly sealed with respect to one another. The inner reservoir 24 is adapted for receiving a first pharmaceutical preparation 28 and the outer reservoir 26 is adapted for receiving a second pharmaceutical preparation 30. It should be understood that the device 10 may be used with any desired pharmaceutical preparations. For example, first pharmaceutical preparation 28 may be an anti-cancer drug, a gene conjugate, a nano-conjugate, insulin or the like. The second pharmaceutical preparation 30 may also be any suitable drug, including drugs that work in conjunction with the first pharmaceutical preparation 28, such as peptides, glycosides, and the like. If the first pharmaceutical preparation 28 is an anti-cancer drug, then second pharmaceutical preparation 30 may be, for example, be a drug for inhibiting cancer cells in the borderline area and/or a drug for protection of healthy cells from infection and side-effects, such as through cancer cell encapsulation via a peptide net around the cancer zone. The two drugs may be selected for conjugation to take place therebetween, with the second pharmaceutical preparation inhibiting migration of the first pharmaceutical preparation to the healthy cells for targeted drug delivery.

An anode 32 and a cathode 34 are each disposed within the hollow housing 12 and are adapted for selective communication with an external electrical power supply (not shown) by respective leads 36, 38. As shown, leads 36, 38 may be bundled together by cord 40 for connection to the external electrical power supply. Alternatively, a battery may be carried on-board for establishing a potential across anode 32 and cathode 34. The anode 32 and the cathode 34 are preferably each respectively received in one of a pair of fluid-tight chambers 50, 52, respectively, defined in the hollow housing 12.

As best shown in FIGS. 1 and 3, a first set of drug delivery needles 42 is mounted to the lower wall 16 of the hollow housing 12 and project outward therefrom. The first set of drug delivery needles 42 are in fluid communication with the inner receptacle 24 for selective delivery of the first pharmaceutical preparation 28 to the patient. Similarly, a second set of drug delivery needles 44 is mounted to the lower wall 16 of the hollow housing 12 and also project outward therefrom. The second set of drug delivery needles 44 is in fluid communication with the outer receptacle 26 for selective delivery of the second pharmaceutical preparation 30 to the patient. The drug delivery needles 42, 44 may each comprise a micro array of micro needles.

Additionally, first and second sets of electrotherapy needles 46, 48, respectively, are also mounted to the lower wall 16 of the hollow housing 12 and project outward therefrom. The first set of electrotherapy needles 46 is in electrical communication with the anode 32 and the second set of electrotherapy needles 48 is in electrical communication with the cathode 34. Corresponding to the rectangular example of housing 12 shown in FIGS. 1-4, the first and second sets of drug delivery needles 42, 44 may each be arrayed in a rectangular grid pattern, for example, and the first and second sets of electrotherapy needles 46, 48 may each be arrayed linearly. Preferably, as shown, chambers 50, 52, which respectively house the anode 32 and the cathode 34, are longitudinally opposed, with the first and second sets of drug delivery needles 42, 44 being positioned between the first and second sets of electrotherapy needles 46, 48.

In use, the combination microarray patch for drug delivery and electrochemotherapy device 10 is pressed against the skin of the patient at the desired drug delivery site such that the first and second sets of drug delivery needles 42, 44, respectively, and the first and second sets of electrotherapy needles 46, 48, respectively, pierce the patient's skin. The medical practitioner then depresses a first region 60 of the flexible upper wall 18 of the hollow housing 12 (indicated by manual force $F_1$ in FIG. 2), which is positioned above the inner receptacle 24, to deliver the first pharmaceutical preparation 28 into the patient through the first set of drug delivery needles 42. The medical practitioner depresses a second region 62 of the flexible upper wall 18 of the hollow housing 12 (indicated by manual force $F_2$ in FIG. 2), which is positioned above the outer receptacle 26, to deliver the second pharmaceutical preparation 30 into the patient through the second set of drug delivery needles 44. It should be understood that the first and second pharmaceutical preparations 28, 30 may be delivered simultaneously. A desired electrical potential may then be selectively pulsed across the anode 32 and the cathode 34 for electroporation to facilitate delivery of one or both of the pharmaceutical preparations. As is well known in the art, particularly in the field of electrochemotherapy, an applied current through the treatment area at the time of drug delivery aids to diffuse and insert the drugs into the cancer cells via electroporation. It should be understood that the applied potential and time of treatment is ultimately dependent upon the particular selection of drugs and the medical condition of the patient. It should be further understood that device 10 may be used with any suitable type of control circuitry, such as those typically associated with electrochemotherapy devices, such as timers, switches, visual indicators and the like.

It is to be understood that the present invention is not limited to the embodiments described above, but encompasses any and all embodiments within the scope of the following claims.

We claim:

1. A combination microarray patch adapted for drug delivery and electrochemotherapy, comprising:
    a hollow housing having a lower wall, an upper wall, a periphery, and at least one sidewall extending between the lower wall and the upper wall about the periphery of the housing, the upper wall being flexible;
    at least one inner wall disposed within the hollow housing, the at least one inner wall dividing an interior region of the hollow housing into an inner drug reservoir and an outer drug reservoir, the inner drug reservoir being adapted for receiving a first pharmaceutical preparation and the outer drug reservoir being adapted for receiving a second pharmaceutical preparation;
    an anode disposed within the hollow housing;
    a cathode disposed within the hollow housing, the anode and the cathode being adapted for connection to an external electrical power supply;
    a first set of drug delivery needles mounted on the lower wall of the hollow housing and projecting outward therefrom, the first set of drug delivery needles being in fluid communication with the inner drug reservoir;
    a second set of drug delivery needles mounted on the lower wall of the hollow housing and projecting outward therefrom, the second set of drug delivery needles being in fluid communication with the outer drug reservoir;
    a first set of electrotherapy needles mounted on the lower wall of the hollow housing and projecting outward therefrom, the first set of electrotherapy needles being in electrical communication with the anode; and
    a second set of electrotherapy needles mounted on the lower wall of the hollow housing and projecting outward therefrom, the second set of electrotherapy needles being in electrical communication with the cathode.

2. The combination microarray patch as recited in claim 1, wherein the inner and outer drug reservoirs are fluidly sealed with respect to one another.

3. The combination microarray patch as recited in claim 1, wherein said anode and said cathode are longitudinally opposed with respect to one another within the hollow housing and are each respectively disposed in one of a pair of fluid-tight chambers defined in said hollow housing.

4. The combination microarray patch as recited in claim 3, wherein said anode and said cathode fluid tight chambers are positioned between the at least one sidewall and a respective outer drug reservoir.

5. The combination microarray patch as recited in claim 4, wherein said first and second sets of drug delivery needles are positioned between said first and second sets of electrotherapy needles.

6. The combination microarray patch as recited in claim 1, wherein said first set of drug delivery needles is arrayed in a rectangular grid pattern.

7. The combination microarray patch as recited in claim 6, wherein said second set of drug delivery needles is arrayed in a rectangular grid pattern.

8. The combination microarray patch as recited in claim 7, wherein said first and second sets of electrotherapy needles are each linearly arrayed.

* * * * *